United States Patent
Kozionov et al.

(10) Patent No.: US 10,840,942 B2
(45) Date of Patent: Nov. 17, 2020

(54) METHOD AND APPARATUS FOR COMPRESSING DATA

(71) Applicant: Siemens Aktiengesellschaft, Munich (DE)

(72) Inventors: Alexey Kozionov, Pskov (RU); Oleg Mangutov, St. Petersburg (RU); Ilya Mokhov, St. Petersburg (RU)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 16/624,642

(22) PCT Filed: Jun. 30, 2017

(86) PCT No.: PCT/RU2017/000475
§ 371 (c)(1),
(2) Date: Dec. 19, 2019

(87) PCT Pub. No.: WO2019/004858
PCT Pub. Date: Jan. 3, 2019

(65) Prior Publication Data
US 2020/0220554 A1    Jul. 9, 2020

(51) Int. Cl.
*H03M 7/30* (2006.01)
*G01M 99/00* (2011.01)
(Continued)

(52) U.S. Cl.
CPC .......... *H03M 7/30* (2013.01); *G01M 99/005* (2013.01); *A61F 2013/15853* (2013.01);
(Continued)

(58) Field of Classification Search
CPC .......... H03M 7/30; H03M 5/00; B63C 11/26; A61N 2005/1034; A61F 2013/15853
(Continued)

(56) References Cited

U.S. PATENT DOCUMENTS

| | | | |
|---|---|---|---|
| 2011/0141845 A1 | 6/2011 | Peacock et al. | |
| 2013/0262049 A1 | 10/2013 | Zhang et al. | |
| 2017/0181098 A1* | 6/2017 | Shinohara | H04W 52/0261 |

FOREIGN PATENT DOCUMENTS

| | | |
|---|---|---|
| CN | 103645052 | 3/2014 |
| WO | WO2013/141741 | 9/2013 |

OTHER PUBLICATIONS

PCT International Search Report dated Apr. 6, 2018 based on PCT/RU2017/000475 filed Jun. 30, 2017.

* cited by examiner

*Primary Examiner* — Joseph J Lauture
(74) *Attorney, Agent, or Firm* — Cozen O'Connor (57) ABSTRACT

Apparatus and a method for compressing data that represent a time-dependent signal that includes a multiplicity of time-dependent signal elements, wherein a multiplicity of spectra are received, where each spectrum corresponds to one of the time-dependent signal elements, and where each spectrum includes a multiplicity of frequencies $f_j$ and a multiplicity of amplitudes of the multiplicity of frequencies, wherein a compressed data record is generated, wherein a respective number of coefficients of an autoregressive model for the multiplicity of amplitudes of each of the multiplicity of frequencies is ascertained, and wherein the compressed data record is generated, where the compressed data record includes at least the number of coefficients and the frequencies associated with the coefficients.

23 Claims, 6 Drawing Sheets

(51) Int. Cl.
 *H03M 5/00* (2006.01)
 *A61N 5/10* (2006.01)
 *B63C 11/26* (2006.01)
 *A61F 13/15* (2006.01)

(52) U.S. Cl.
 CPC ....... *A61N 2005/1034* (2013.01); *B63C 11/26* (2013.01); *H03M 5/00* (2013.01)

(58) Field of Classification Search
 USPC ................... 341/87, 50; 367/134; 703/2, 6
 See application file for complete search history.

| | $t_1$ | $t_2$ | $t_3$ | $t_4$ | $t_5$ |
|---|---|---|---|---|---|
| $f_1$ | $a_{1,1}$ | $a_{1,2}$ | $a_{1,3}$ | $a_{1,4}$ | $a_{1,5}$ |
| $f_2$ | $a_{2,1}$ | $a_{2,2}$ | $a_{2,3}$ | $a_{2,4}$ | $a_{2,5}$ |
| $f_3$ | $a_{3,1}$ | $a_{3,2}$ | $a_{3,3}$ | $a_{3,4}$ | $a_{3,5}$ |
| $f_4$ | $a_{4,1}$ | $a_{4,2}$ | $a_{4,3}$ | $a_{4,4}$ | $a_{4,5}$ |
| $f_5$ | $a_{5,1}$ | $a_{5,2}$ | $a_{5,3}$ | $a_{5,4}$ | $a_{5,5}$ |
| $f_6$ | $a_{6,1}$ | $a_{6,2}$ | $a_{6,3}$ | $a_{6,4}$ | $a_{6,5}$ |

METHOD AND APPARATUS FOR COMPRESSING DATA

CROSS-REFERENCE TO RELATED APPLICATIONS

This is a U.S. national stage of application No. PCT/RU2017/000475 filed Jun. 30, 2017.

BACKGROUND OF THE INVENTION

1. Field of the Invention

The invention relates to a computer program product, a signal processing unit and a method for compressing data that represent a time-dependent signal, wherein the time-dependent signal comprises a multiplicity of time-dependent signal elements, where the method comprises receiving a multiplicity of spectra, where each spectrum corresponds to one of the time-dependent signal elements and where each spectrum comprises a multiplicity of frequencies and a multiplicity of amplitudes of the multiplicity of frequencies, and the method further comprises generating a compressed data record.

2. Description of the Related Art

The compression of data plays an important part in the management of large volumes of data. For example, large volumes of data accumulate in modern technical systems for monitoring the technical system. Management of the data, part of which occurs at the location of the technical system and another part of which occurs remotely therefrom, comprises storage and transmission of the data. Efficient data management is achievable by intelligent data compression technologies, as a result of which firstly the storage space required for storing the data can be reduced and the bandwidth required for transmitting the data can be reduced.

In the case of a continual data stream that represents a time-dependent signal collected during uninterrupted monitoring of a technical system, e.g., the vibration monitoring of a machine, during operation thereof, the processing and storage of Fourier transformations, i.e., spectra of the time-dependent signal, requires a large amount of memory space. Standard methods of compressing data spectra comprise, e.g., universal lossless compression tools (such as ZIP) or the use of memory-optimized coding. The compression rates, i.e., the ratio of the memory space required for storing the compressed data relative to the memory space for the measurement data, is comparatively low, however. There is therefore a need for improved methods for compressing data.

WO 2013/141741 A1 discloses a method for compressing data that represent a time-dependent signal, where the time-dependent signal comprises a multiplicity of time-dependent signal elements. This method involves a multiplicity of spectra being received, where each spectrum corresponds to one of the time-dependent signal elements. Each spectrum comprises a multiplicity of frequencies and a multiplicity of amplitudes of the multiplicity of frequencies. The multiplicity of amplitudes is normalized for each spectrum to obtain normalized amplitudes. The normalized amplitudes are processed, based on a distribution of the normalized amplitudes in view of different threshold values. On that basis, a compressed data record is generated.

SUMMARY OF THE INVENTION

It is an object of the invention to provide a method for compressing data and a signal processing unit that further increase the compression of the data.

These objects are achieved by a a signal processing unit and a method for compressing data $D(nT)$ that represent a time-dependent signal $A(t)$. The time-dependent signal $A(t)$ comprises a multiplicity of time-dependent signal elements $A_i(t)$. Initially, a multiplicity of spectra $S_i(f)$ are received, where each spectrum $S_i(f)$ corresponds to one of the time-dependent signal elements $A_i(t)$. Each spectrum $S_i(f)$ comprises a multiplicity of frequencies $f_j$ and a multiplicity of amplitudes $a_{j,i}$ of the multiplicity of frequencies $f_j$. Further, a compressed data record is generated. The method is distinguished in that a respective number of coefficients of an autoregressive model for the multiplicity of amplitudes $a_{j,i}$ of each of the multiplicity of frequencies $f_j$ is ascertained. Thereafter, the compressed data record is generated, where the compressed data record comprises at least the number of coefficients and the frequencies $f_j$ associated with the coefficients.

The compressed data record can be used to severely reduce large volumes of data. This involves the memory space required for storing the data being severely reduced. Further, the bandwidth required for transmitting the captured data in the form of the compressed data record is low, which means that further processing of the data contained in the compressed data record can occur at a different location than the capture.

In accordance with one expedient embodiment, a timestamp $t_i$ is generated for each of the time-dependent signal elements $A_i(t)$. The timestamp $t_i$ represents a time at which the respective time-dependent signal element $A_i(t)$ was captured. The timestamp $t_i$ can be used to ascertain the order of occurrence of the time-dependent signal elements $A_i(t)$. This allows indexing of the multiplicity of amplitudes $a_{j,i}$ for each spectrum and subsequent processing of the amplitudes for the purpose of ascertaining a respective number of coefficients.

In accordance with a further expedient embodiment, the number of coefficients is varied based on a classification value.

The classification value represents a state of health of a technical system. The classification value is ascertained by processing the spectra $S_i(f)$. The technical system may be, by way of example, a motor or a turbine. The state of health of the technical system indicates whether the technical system behaves normally or is in an unusual state. An unusual state of this kind could be, by way of example, the occurrence of unusual or disproportionately high vibrations and the like.

In accordance with a further expedient embodiment, a the classification value is ascertained by comparing the multiplicity of spectra $S_i(f)$ with at least one threshold value. The at least one threshold value may have been stipulated in advance by experiments or numerical ascertainment. By way of example, one or more threshold values can be used to stipulate whether vibrations in a technical system are in a standard range, in a still tolerable range or in a no longer tolerable range.

In accordance with a further expedient embodiment, a first classification value, which represents a first, in particular defective, state of health of the technical system, prompting a first, in particular high, number of coefficients is ascertained. This ensures that the number of coefficients can be used for the most accurate possible reproduction of the spectra ascertained from the time-dependent signal.

In accordance with a further embodiment, a second classification value, which represents a second, in particular non-defective, state of health of the technical system, prompts a, in comparison with the first number, lower second number of coefficients to be ascertained. As a result, when the state of health of the technical system is "good", it is possible for a comparatively coarse reproduction of the multiplicity of spectra using a comparatively small number of classification values to occur, which means that the extent of the data available following performance of the determination of the number of coefficients of a regressive model can be reduced to a maximum degree.

In other words, this means that the compression ratio is adjusted based on the state of health of the technical system. When the technical system is in a defective state, a low compression ratio is chosen, whereas when the technical system behaves normally, the compression ratio is chosen to be high. This ultimately allows, when the compression of the data is considered over a longer period, compression of the data to the maximum possible degree.

In accordance with a further expedient embodiment, the first and/or the second number of coefficients of the autoregressive model is determined by the Akaike information criterion (AIC).

In accordance with one alternative embodiment, the first and/or the second number of coefficients of the autoregressive model is determined by the Bayesian information criterion (BIC).

In accordance with a further alternative embodiment, the first and/or the second number of coefficients of the autoregressive model is determined such that the first and/or second number of coefficients corresponds to the number of frequencies $f_j$. The latter can be effected manually by an operator.

In accordance with a further expedient embodiment, as a further step, the ascertainment of reconstructed data D'(nT) from the compressed data record is performed. In order to be able to assess the Q factor of the compression, there may furthermore be provision for a correlation coefficient between the data D(nT) and the reconstructed D'(nT) to be ascertained. The correlation coefficient can be ascertained during the monitoring of the technical system, this then occurring particularly before the transmission of the compressed data to a remote computation unit. If a reconstruction of the data D(nT) with insufficient consistency is obtained from the reconstructed data D'(nT), then the compression can be repeated using a larger number of coefficients. Fundamentally, the correlation coefficient can also be used to optimize the compression method in advance, so that an already suitable number of correlation coefficients is determined based on the state of health.

In accordance with a further expedient embodiment, a projected spectrum $S_i'(f)$ is ascertained from the number of coefficients in the compressed data record per timestamp $t_i$. The projected spectrum $S_i'(f)$ can then be used to analyze the technical system. On the condition that there is a sufficiently good correlation with the spectra ascertained from the data D(nT), it is possible for a qualified appraisal of the state of the technical system to be made.

In accordance with a further expedient embodiment, the projected spectrum $S_i'(f)$ is ascertained for at least one of the timestamps $t_i$. In particular, there may be provision for the projected spectrum $S_i'(f)$ to be ascertained for each of the timestamps $t_i$.

It is also an object of the invention to provide a computer program product (i.e., a non-transitory computer-reliable medium) that can be loaded directly into the internal memory of a digital signal processing unit and that comprises software code sections that are used to implement the steps of the method in accordance with disclosed embodiments of the invention when the product runs on the signal processing unit. The computer program product may be realized in the form of a DVD, a CD-ROM, a USB memory stick and the like. However, the computer program product may also be available as a stored program that can be loaded wirelessly or via a wired connection.

It is also an object of the invention to provide a signal processing unit that is configured to compress data D(nT) in accordance with the disclosed embodiments of the method of the invention. The signal processing unit comprises a reception unit, an autoregressive coefficient determination unit and a memory unit. The reception unit receives the multiplicity of spectra $S_i(f)$. The autoregressive coefficient determination unit determines a respective number of coefficients of an autoregressive model for the multiplicity of amplitudes $a_{j,i}$ of each of the multiplicity of frequencies $f_j$. The memory unit stores the compressed data record.

In accordance with one expedient embodiment, the signal processing unit further comprises a correlation unit for determining a correlation coefficient between the data D(nT) and the reconstructed data D'(nT).

In accordance with a further expedient embodiment, the signal processing unit comprises a spectrum unit for each of the time-dependent signals $A_i(t)$ for computing the respective spectrum $S_i(f)$.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention for compressing data that represent a time-dependent signal $A_i(t)$ will now be described with reference to the attached drawings. The drawings and the embodiments described below are used to describe an exemplary embodiment, but are not restricted thereto. In the figures below, like elements are provided with like reference symbols, in which.

DETAILED DESCRIPTION OF THE EXEMPLARY EMBODIMENTS

Figure 1:
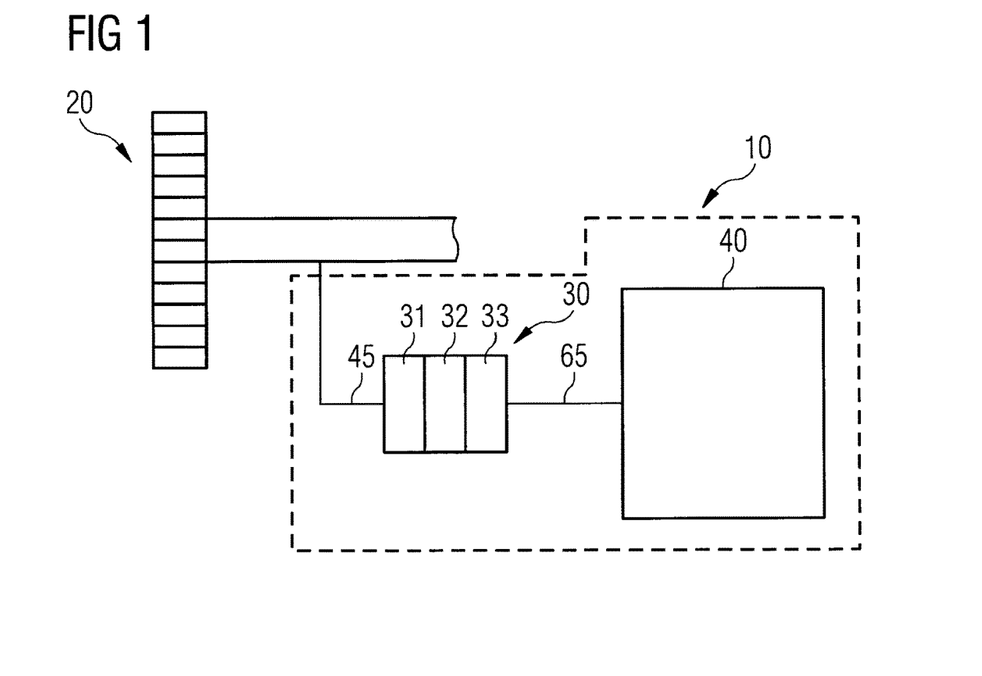
FIG. 1 shows a schematic depiction of a state monitoring system that comprises a data capture unit and a signal conditioning unit.

FIG. 1 shows a state monitoring system 10 for monitoring the health of a technical system 20, e.g. a motor.

The state monitoring system 10 comprises a data capture unit 30 and a signal processing unit 40. The data capture unit 30 captures a time-dependent signal A(t) 45, which is a continual signal (characterized by the independent time variable "t") that relates, for example, to vibrations of the motor 20. The data capture unit 30 provides the signal processing unit 40 with data D(nT) 65. The data D(nT) 65 are a discrete-time (characterized by the independent variable "nT") representation of the time-dependent signal A(t) 45, which is progressively processed in order to compress the data D(nT) 65.

The data capture unit 30 comprises a sensor 31, a signal conditioning unit 32 and an analog-to-digital converter 33 (ADC). The sensor 31 captures the time-dependent signal A(t) 45 and makes it available to the signal conditioning unit 32 for processing. The signal conditioning unit 32 conditions the time-dependent signal A(t) 45 and makes a conditioned, time-dependent signal A'(t) available to the analog-to-digital converter 33. The analog-to-digital converter 33 digitizes the conditioned time-dependent signal A'(t), as a result of which the data D(nT) 65 are generated. These are provided to the signal processing unit 40, where the data D(nT) 65 represent the time-dependent signal A(t).

The time-dependent signal A(t) 45 can be captured persistently (continually) by the data capture unit 30. The latter can be regarded as a multiplicity of time-dependent signal elements $A_i(t)$ (where i=1, ..., NoS) 46-50 (cf. FIG. 2). The time-dependent signal elements $A_i(t)$ can be regarded as the time-dependent signal A(t) 45 captured during a multiplicity of different time intervals $\Delta t_i$ (where i=1, ..., NoS) 51-55 or as a time-dependent signal A(t) 45 provided with windows in a time domain, where the window intervals correspond to the time intervals $\Delta t_i$ 51-55.

Figure 2:
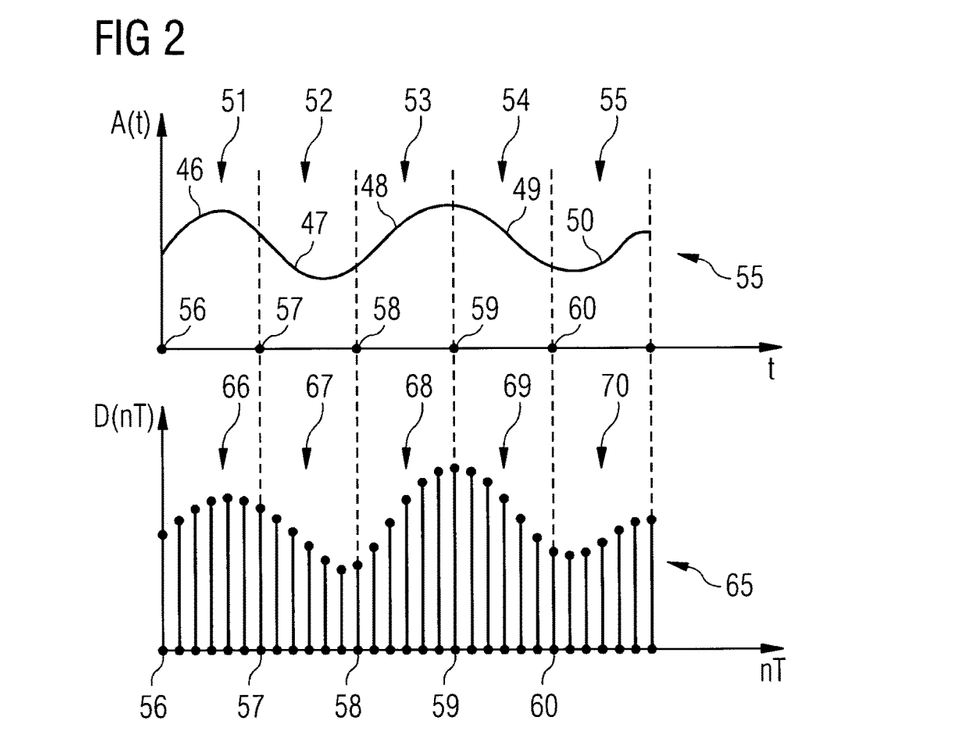
FIG. 2 shows data that represent a time-dependent signal.

Alternatively, the data capture unit 30 can capture the time-dependent signal A(t) 45 during the time intervals $\Delta t_i$ 51-55 using a time domain provided with windows, as a result of which the time-dependent signal A(t) 45 can be regarded as a successive capture of the signal elements $A_i(t)$ 46-50.

The periods of the time intervals $\Delta t_i$ 51-55 may have been defined by a user or be defined in a fixed or variable manner, depending on the type of the time-dependent signal A(t) 45, signal processing requirements, properties of the data capture unit 30 and/or of the signal processing unit 40, etc. The periods may be microseconds, milliseconds or seconds. The time intervals $\Delta t_i$ 51-55 are always contiguous. They could, however, also overlap or be separated from one another by particular time spans.

In the present disclosure, the term "signal element" is defined as a section of the time-dependent signal A(t) 45 that has been captured by the data capture unit 30 during respective time intervals $\Delta t_i$ 51-55.

In this disclosure, "NoS" is a dimensionless unit and relates to a cardinal number of the signal elements $A_i(t)$ 46-50 that have been captured during the time intervals $\Delta t_i$ 51-55 and in total form the time-dependent signal A(t) 45. In other words, NoS represents the number of signal elements $A_i(t)$.

A multiplicity of timestamps $t_i$ (where i=1, NoS) 56-60 from the time-dependent signal A(t) 45 are determined, wherein each timestamp $t_i$ 56-60 represents a starting time for a respective signal element $A_i(t)$ 46-50 that has been captured during the time intervals $\Delta t_i$ 51-55. For example, the timestamp $t_1$ 56 denotes the starting time for the signal element $A_1(t)$ 46.

The data D(nT) 56 are a discrete-time representation of the time-dependent signal A(t) 45. For this reason, the signal elements $A_i(t)$ 46-50 result in a multiplicity of discrete-time signal elements $D_i(nT)$ (i=1, ..., NoS; n=1, ..., NoP) 66-70 (see FIG. 2, lower graph), where the data elements $D_i(nT)$ 66-70 are consistent with the data D(nT) 65 that are available in the time intervals $\Delta t_i$ 51-55. The data elements $D_i(nT)$ 66-70 can likewise be obtained via discrete-time "domain windowing" of the time-dependent signal A(t) 45. For this reason, the data D(nT) 65 comprise discrete-time representations of the multiplicity of signal elements $A_i(t)$ 51-55, i.e., the data elements Di(nT) 66-70. Furthermore, the data D(nT) 65 may also be a digital representation of the discrete-time equivalent of the time-dependent signal A(t) 45.

In this description, "NoP" is a dimensionless unit and relates to a cardinal number of the samples that are contained in each discrete-time signal element $D_i(nT)$ 66-70. "NoP" is likewise consistent with a cardinal number of the frequencies that is determinable by an NoP-point discrete Fourier transformation (DFT) that has been applied to the data elements $D_i(nT)$ 66-70.

"NoP" can be varied for the data elements $D_i(nT)$ 66-70 by varying the sampling rate of the analog-to-digital converter 33. "NoP" can also be modified by zero padding, as well as the duration of the time intervals $\Delta t_i$ 51-55 being able to be changed on the basis of the effect of a change of "NoP". A variation of "NoP" accordingly varies the cardinal number of the frequencies that is determinable by an NoP-point DFT.

The timestamps $t_i$ 56-60 likewise represent the time of the start of the data elements $D_i(nT)$ 66-70. Therefore, the timestamps $t_i$ 56-60 comprise information regarding the time of capture of the data elements $D_i(nT)$ 66-70, i.e., the starting time for the time intervals $\Delta t_i$ 51-55, and are therefore advantageous for the compression of the data D(nT) 65, as well as for the reconstruction of the data D(nT) 65. The timestamps $t_i$ 56-60 can also represent periods for which respective signal elements $A_i(t)$ and data elements $D_i(nT)$ have been captured.

Figure 3:
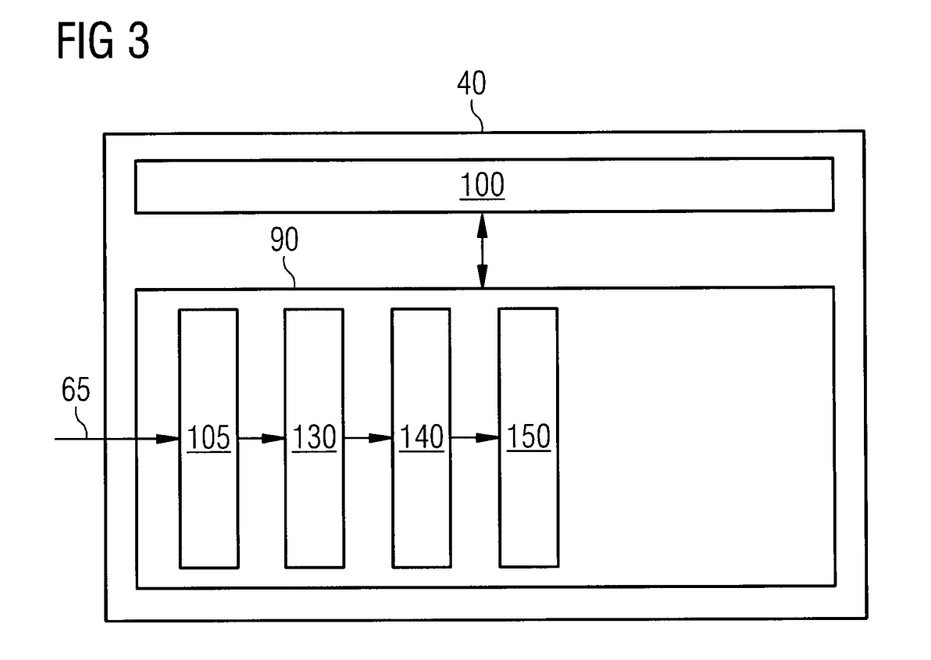
FIG. 3 shows various units of a signal conditioning unit.

The signal processing unit 40, which is depicted schematically in FIG. 3, comprises a processor 90 and a memory unit 100 for storing compressed data. For the further explanations, NoP=6 and NoS=5 are chosen in FIG. 4.

The processor 90 comprises a spectrum unit 105, a spectral data reception unit 130, an autoregressive coefficient determination unit 140 and an optional correlation unit 150. The aforementioned units 105, 130, 140 and 150 are configured to compress the data D(nT).

Figure 4:
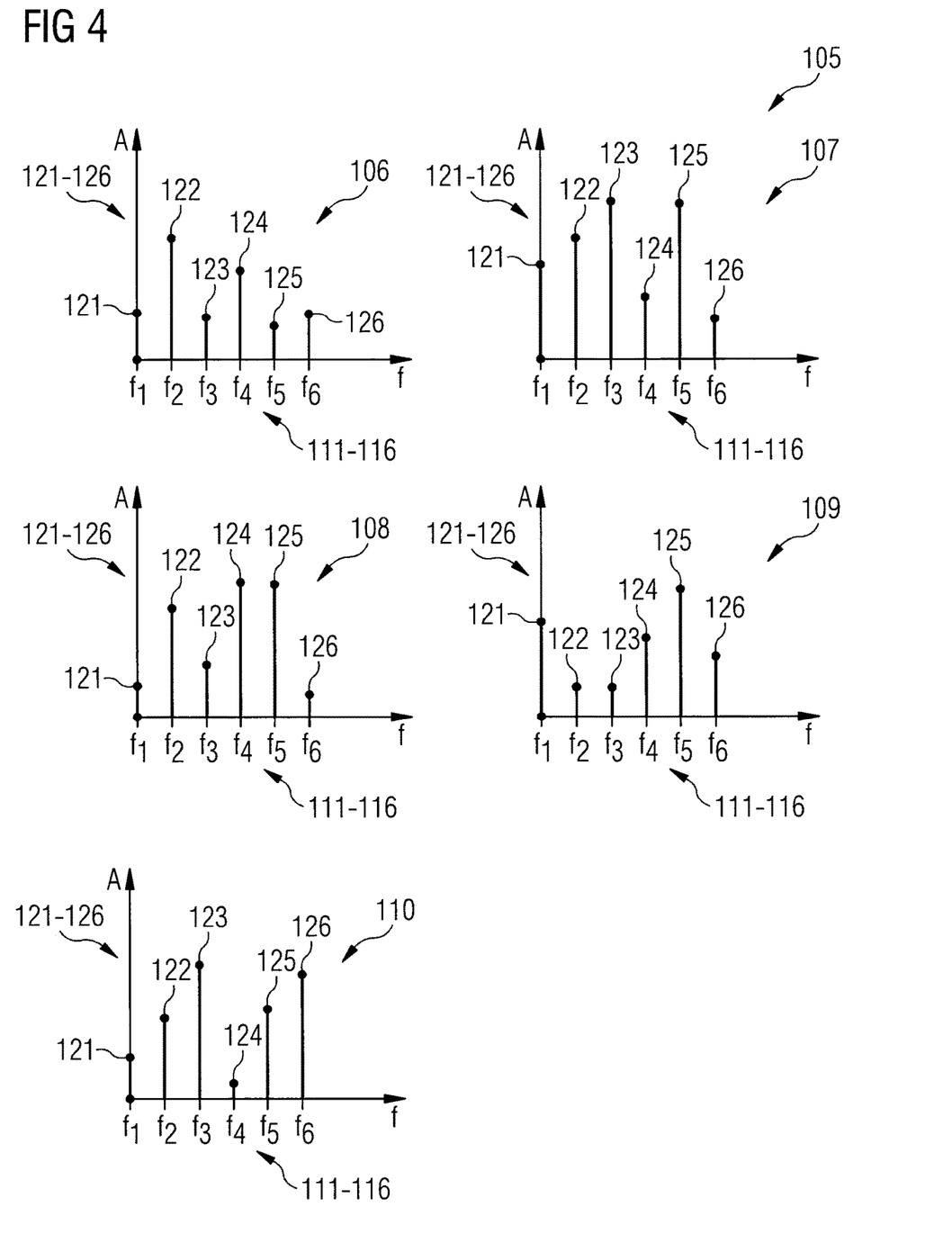
FIG. 4 shows a multiplicity of spectra.

The spectrum unit 105 receives the data elements $D_i(nT)$ 66-70 and computes a multiplicity of spectra $S_i(f)$ (where i=1, ..., NoS) 106-110. The spectrum unit 105 computes the spectra $S_i(f)$ 106-110 as a multiplicity of NoP-point (discrete Fourier transformations) DFTs. The multiplicity of spectra $S_i(f)$ 106-110 comprises a multiplicity of frequencies $f_j$ (where j=1, ..., NoP) 111-116 and a multiplicity of amplitudes $a_{j,i}$ (where j=1, ..., NoP; i=1, ..., NoS) 121-126 of the frequencies $f_j$ 111-116. The computed amplitudes $a_{j,i}$ 121-126 are associated with the frequencies $f_j$ 111-116 and scales of the proportions of the multiplicity of the frequencies $f_j$ 111-116 in the signal elements $A_i(t)$ 46-50. The association of the amplitudes $a_{j,i}$ 121-126 with frequencies $f_j$ 111-116 is a definition that a person skilled in the art knows for a spectrum of a time-dependent signal, i.e., the amplitudes are a measurement of the proportion of the associated frequency with respect to the subordinate time-dependent signal.

Schematic operation of the spectrum unit 105 is identified by "105" in FIG. 4. For each spectrum $S_i(f)$ 106-110, the horizontal axis "f" represents a "frequency" ($f_j$ 111-116). The vertical axis "A" represents an "amplitude", i.e., the amplitudes $a_{j,i}$ 121-126 of the frequencies $f_j$ 111-116 of the underlying time-dependent signal A(t).

The operation of the spectrum unit 105 is explained below. The data elements $D_i(nT)$ 66-70 are received by the signal processing unit 40 and buffer-stored as data blocks of a particular length in the memory unit 100. Each data block corresponds to each of the data elements $D_i(nT)$ 66-70 that has been captured during each of the time intervals $\Delta t_i$ 51-55. Each data block is provided with a respective timestamp $t_i$ 56-60 for identifying the starting time of the capture of the data elements $D_i(nT)$ 66-70. The data blocks that correspond to the data elements $D_i(nT)$ 66-70 are then received and processed for the purpose of computing the spectra $S_i(f)$ 106-110.

In the presently contemplated exemplary embodiment, the amplitudes $a_{j,i}$ 121-126 and the frequencies $f_j$ 111-116 of the spectra $S_i(f)$ 106-110 are depicted as two dimensional amplitude arrays 128 (cf. FIG. 5) that comprise rows and columns. By way of example, the array shown in FIG. 5 comprises NoP rows, which represent the NoP $f_j$ 111-116 frequencies, and NoS columns, which represent the NoS data elements $D_i(nT)$ 66-70.

Each of the spectra $S_i(f)$ 106-110 is computed by respective data elements $D_i(nT)$ 66-70. For this reason, "NoS" also represents the number of spectra.

The spectral data reception unit 130 receives the spectra $S_i(f)$ 106-110 from the spectrum unit 105. The spectral data reception unit 130 generates a vector of the amplitudes $a_{j,i}$ 121-126 and one of the frequencies $f_j$ 111-116 contained in the spectra $S_i(f)$ 106-110. This associates a vector $a_{j,i}$ 121-126 with a respective timestamp $t_i$ 65-60.

Figure 5:
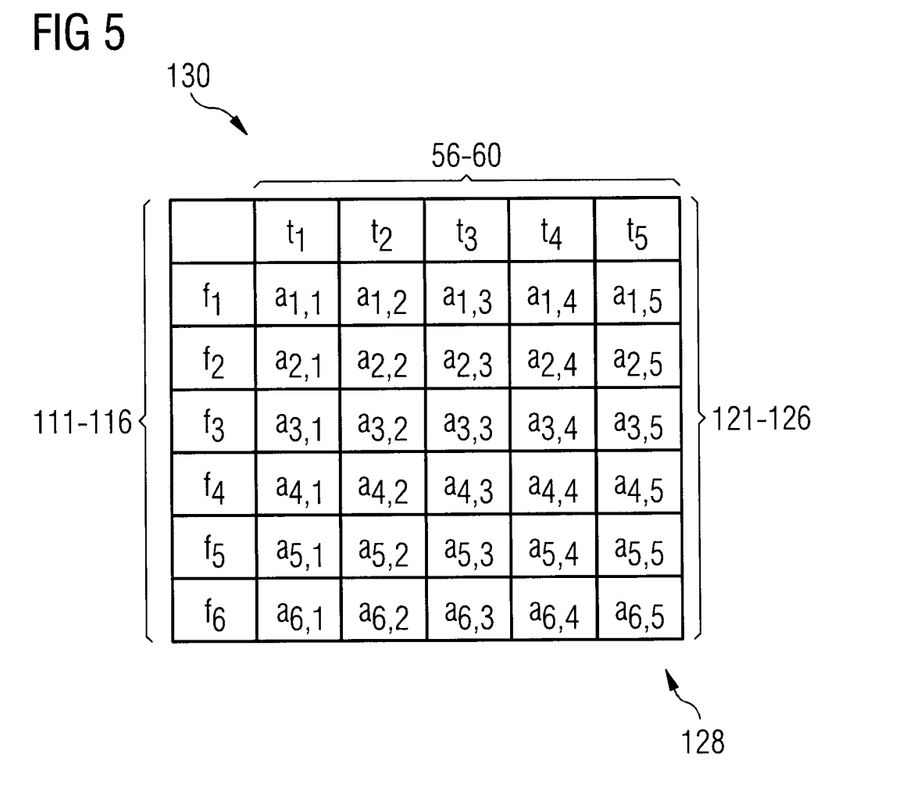
FIG. 5 shows an amplitude array.

In the amplitude array 128, each column "i" of the NoS columns is denoted by a respective timestamp $t_i$ 65-60 that corresponds to the respective data elements $D_i(nT)$ 66-70. Correspondingly, each row "j" of the NoP rows is denoted by a respective frequency $f_j$ 111-116. For example, the first column is identified by the timestamp $t_1$ 56 and contains all amplitudes $a_{j,i}$ 121-126 of the frequencies $f_j$ 111-116 that have been computed from the spectra $S_1(f)$ 106. Correspondingly, the first row is identified by $f_1$ 111 and contains all amplitudes $a_{j,i}$ 121-126 of the frequency $f_1$ 111 that have been computed from the number of spectra $S_i(f)$ 106-110.

FIG. 5 shows an example of the amplitude array 128 for five spectra $S_i(f)$ 106-111 (NoS=5) and six frequencies $f_j$ 111-116 (NoP=6), as is generated by the spectral data reception unit 130. The column values $a_{1,1}$ 121 to $a_{6,1}$ 126 represent, by way of example, the values of the six frequencies $f_1$ 111 to $f_6$ 116 that have been determined by the spectrum $S_1(f)$ 106 and computed for the data elements $D_1(nT)$ 66 with the timestamp $t_1$ 56. The column values $a_{3,1}$ 123 to $a_{3,5}$ 123 represent the values of the third frequency $f_3$ 113 that have been determined by the spectrum $S_1(f)$ 106 to $S_5(f)$ 110 and respectively computed for the data elements $D_1(nT)$ 66 to $D_5(nT)$ 70 and each bear the timestamp $t_1$ 56 to is 60.

Figure 6:
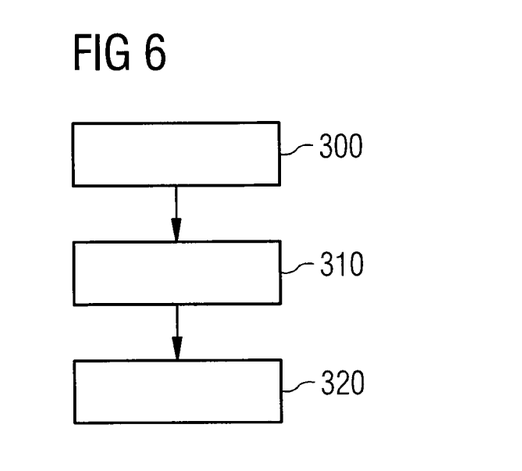
FIG. 6 shows a flowchart that illustrates the various method steps of the method in accordance with the invention.

The volume of data accumulating in the process can assume a very large extent. In order to be able to reduce the memory space required for storage, but also the bandwidth required for transmission, there is provision for compression. After the amplitude array 128, as described above, has been ascertained, the method described in FIG. 6 is now used to perform the further processing.

In a step 300, the spectra $S_i(f)$ 106-110 are ascertained, as described above, so that the multiplicity of amplitudes $a_{j,i}$ 121-126 of each of the multiplicity of frequencies $f_j$ 111-116 is available for each timestamp $t_i$ 56-60.

A step 310 involves a respective number of coefficients of an autoregressive model for the multiplicity of amplitudes $a_{j,i}$ 121-126 of each of the multiplicity of frequencies $f_j$ 111-116 being ascertained for each spectrum $S_i(f)$ 106-110. This means that the number of coefficients of the chosen autoregressive model is computed for the column values $a_{1,1}$ 121 to $a_{6,1}$ 126, that the values of the six frequencies $f_1$ 111 to $f_6$ 116 that have been determined for the spectrum $S_1(f)$ 106, for the data elements $D_1(nT)$ 66 and for the timestamp $t_1$ 56. Correspondingly, a corresponding procedure is used for the further spectra $S_2(f)$ 107 to $S_5(f)$ 110.

In a step 320, the entirety of the coefficients of the autoregressive model is stored in the memory unit 100 as a compressed data record CDS. Alternatively or additionally, the ascertained coefficients of the autoregressive model for the multiplicity of amplitudes $a_{j,i}$ 121-126 of each of the multiplicity of frequencies $f_j$ 111-116 of the spectra $S_i(f)$ 106-110 (i.e., the compressed data record CDS) can also be transmitted via a communication link, which is not shown in the figures, to a receiver, which is likewise not shown, for storage and further processing.

Further analysis requires all of the accumulating data (i.e., the autoregressive coefficients ascertained using the method above). Consequently, it is possible for this, sometimes still substantial, volume of data to be further reduced using the method described in FIG. 7. This further reduction is based on a classification value that represents a state of health of the technical system. This is ascertained by processing the spectra $S_i(f)$ 106-110 ascertained in step 300. Adaptation of the compression rate, which can be influenced via the chosen number of coefficients of the autoregressive model for the multiplicity of amplitudes of each of the multiplicity of frequencies, is then performed based on the classification value.

Figure 7:
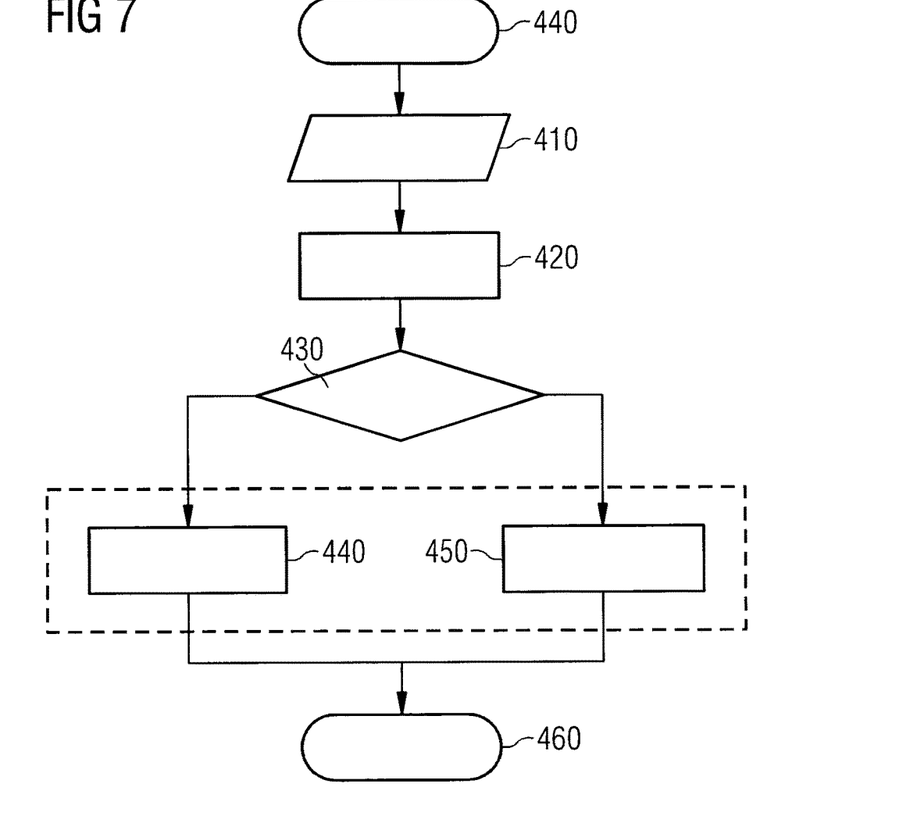
FIG. 7 shows a flowchart that illustrates a further sub-aspect of the method in accordance with the invention as a flowchart.

The adaptation method starts with step 400. In step 410, the number of spectra $S_i(f)$ 106-110 and the resultant amplitude array 128 are determined, as has been explained above. In step 420, the classification value is determined by comparing the multiplicity of spectra $S_i(f)$ 106-110 with a threshold value. The threshold value may have been determined beforehand by experiments or numerical simulation. The threshold value can be used to stipulate whether the technical system has a fault, e.g., excessively strong vibrations of the motor 20, or whether the technical system is in a fault-free state. To this end, it is possible to stipulate a first classification value that represents a first, defective state of health of the technical system, i.e., the motor 20. A second classification value may be associated with a second, fault-free state of health of the technical system, i.e., the motor 20.

In step 430, a check is performed to determine which of the classification values is available. If the first classification value is available, then a defective state of health of the technical system is inferred and the method continues with step 440. If the second classification value has been ascertained, which represents the second, non-defective (i.e., fault-free) state of health of the technical system, then the method continues with step 450.

In step 440, which is performed when there is a first, defective state of health of the technical system, a first, high number of coefficients of the autoregressive model for the multiplicity of amplitudes $a_{j,i}$ 121-126 of each of the multiplicity of frequencies $f_j$ 111-116 is ascertained. This attains a comparatively lower compression rate for the data D(nT) that are to be compressed.

In step 450, which is performed when there is the second, non-defective state of health of the technical system, a second number of coefficients of the autoregressive model for the multiplicity of amplitudes $a_{j,i}$ 121-126 of each of the multiplicity of frequencies $f_j$ 111-116 is ascertained, where the second number of coefficients is (substantially) lower in comparison with the first number of coefficients. This attains a comparatively higher compression rate.

Although the present exemplary embodiment has been provided merely to distinguish between a defective and a non-defective state of health of the technical system, the definition of a plurality of threshold values allows finer grading of different fault states of the technical system to be performed. The scale of the state of health is then taken as a basis for choosing the number of coefficients of the autoregressive model for the multiplicity of amplitudes $a_{j,i}$ 121-126 of each of the multiplicity of frequencies $f_j$ 111-116.

Following the determination of the coefficients of the autoregressive model for the multiplicity of amplitudes $a_{j,i}$ 121-126 of each of the multiplicity of frequencies $f_j$ 111-116, the method ends at step 460.

The first and/or the second number of coefficients of the autoregressive model can be determined in different ways. To this end, it is possible, for example, to use the known Akaike information criterion (AIC) or the known Bayesian information criterion (BIC). Similarly, manual judgement by an operator is possible, the operator being able to choose the arrangement, i.e., the number of coefficients of the autoregressive model, such that the number corresponds to the number of frequencies $f_j$. In the previously described exemplary embodiment, this would correspond to the number "6".

Figure 8:
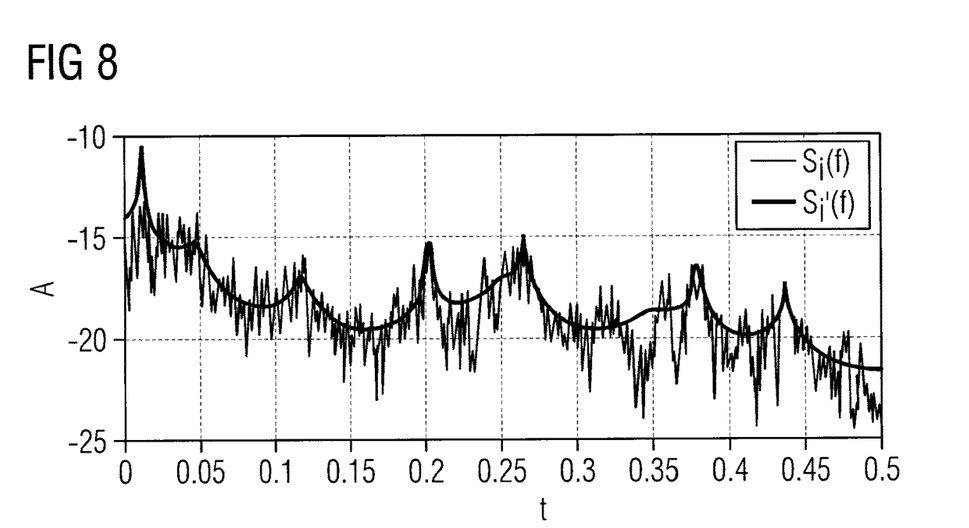
FIG. 8 shows the time profile of a time-dependent FFT amplitude of measurement data and compressed data.

In order to be able to perform a data analysis and visualization of the compressed data from the coefficients of the autoregressive model (i.e., the compressed data record CDS), the spectra can be reconstructed from the coefficients for a respective timestamp $t_i$ 56-60. To this end, a projected spectrum $S_i'(f)$ is ascertained from the number of coefficients in the compressed data record CDS per timestamp $t_i$ 56-60. This reconstruction can be used particularly also for denoising the original spectrum $S_i(f)$ 106-110. An exemplary embodiment is shown in FIG. 8, which illustrates the amplitude A of the ascertained spectrum $S_i(f)$ in comparison with the reconstructed spectrum $S_i'(f)$ for a timestamp $t_i$. It can clearly be seen that the reconstructed spectrum $S_i'(f)$ corresponds to a projection of the originally ascertained spectrum $S_i(f)$. The projection is all the more accurate the larger the number of coefficients of the autoregressive model that has been chosen for compression.

This approach described here can be used for any spectrum $S_i(f)$ for any timestamp $t_i$.

Figure 9:
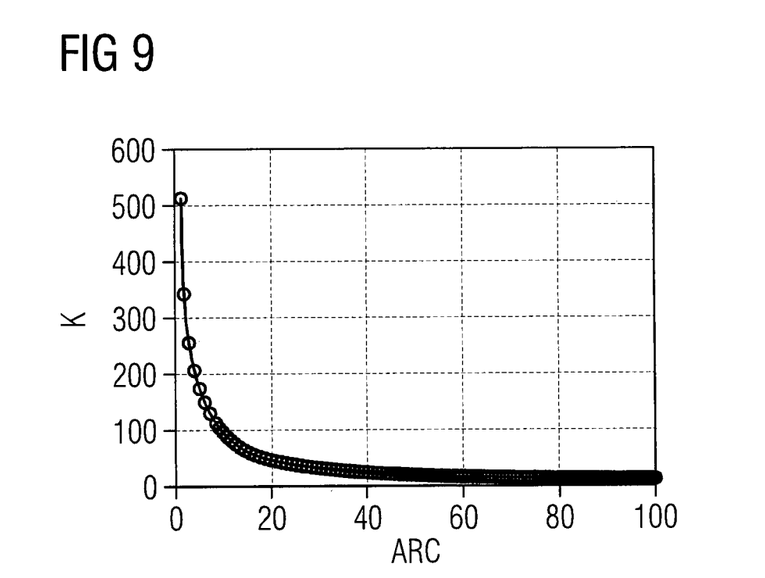
FIG. 9 shows a compression ratio that illustrates the compression on the basis of the number of autoregressive coefficients.
Figure 10:
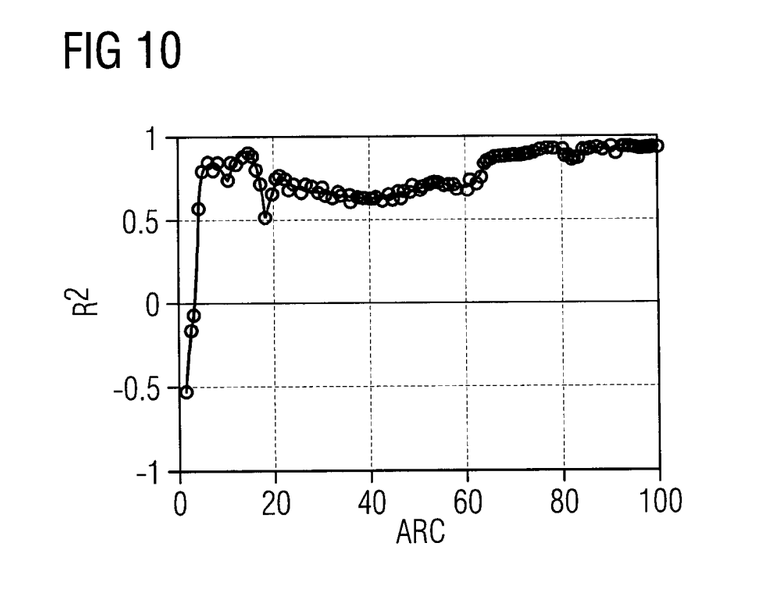
FIG. 10 shows the profile of the $R^2$ coefficient based on the number of correlation coefficients.

FIGS. 9 and 10 show the efficiency of the proposed method by way of example. The efficiency of the method is judged by a compression coefficient K and what is known as the "coefficient of determination" $R^2$.

The compression coefficient K is the ratio of the initial number of input values to the number of values that need to be stored after compression. The compression coefficient Kcan therefore be computed from the ratio of the size of the input data to the size of the compressed data. This results, on the basis of the number of coefficients ARC of the regressive model, in the profile shown in FIG. 9, where the compression coefficient K is depicted over the number of coefficients ARC used for the compression.

$R^2$ indicates how well data points fit into a statistical model, such as a line or curve. $R^2$ is determined in accordance with the following relationship:

$$R^2 = 1 - \frac{V((y|x))}{V(y)} = 1 - \frac{\sigma^2}{\sigma_y^2}$$

Here, $\sigma$ denotes the variance in the model error of a model and $\sigma_y$ denotes the variance in the real spectrum $S_i(f)$. FIG. 10 shows the coefficient $R^2$ over the number of coefficients ARC used for the compression. From this, it can clearly be seen that a significant compression of the spectrum is obtained with just a small number of coefficients ARC of the autoregressive model.

The proposed method allows adaptive compression that is based on the actual state of the technical system to be monitored. The compression of the spectra ascertained in a known manner by representation using a number of coefficients of an autoregressive model allows high compression rates. At the same time, the reconstruction of the originally determined spectra from the number of coefficients of the autoregressive model can involve filtering being performed, with the filter strength resulting from the number of coefficients previously used for the compression.

The data compressed using the method described can be stored as a compressed data record CDS and/or transmitted to another computation unit for further processing.

Thus, while there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for compressing data representing a time-dependent signal comprising a multiplicity of time-dependent signal elements, the method comprising:

receiving, by a digital signal processing unit having a processor and a memory unit, a multiplicity of spectra, each spectrum of the multiplicity of spectra corresponding to one time-dependent signal element of the time-dependent signal elements, and each spectrum comprising a multiplicity of frequencies and a multiplicity of amplitudes of the multiplicity of frequencies;

generating, within the digital processing processor, a compressed data record;

ascertaining, within the digital processing processor, a respective number of coefficients of an autoregressive model for a multiplicity of amplitudes of each of the multiplicity of frequencies; and generating the compressed data record, said compressed data record comprising at least a number of coefficients and the frequencies associated with the coefficients.

2. The method as claimed in claim 1, further comprising:
generating a timestamp for each of the time-dependent signal elements;
wherein the timestamp represents a time at which the respective time-dependent signal element was captured.

3. The method as claimed in claim 2, wherein the number of coefficients is varied based on a classification value; wherein the classification value represents a state of health of a technical system and is ascertained by processing the multiplicity of spectra.

4. The method as claimed in claim 1, wherein the number of coefficients is varied based on a classification value; wherein the classification value represents a state of health of a technical system and is ascertained by processing the multiplicity of spectra.

5. The method as claimed in claim 4, further comprising:
comparing the multiplicity of spectra with at least one threshold value to ascertain the classification value.

6. The method as claimed in claim 5, further comprising:
prompting a first, high number of coefficients to be ascertained by a first classification value, which represents a first, defective, state of health of the technical system.

7. The method as claimed in 5, further comprising:
prompting a, in comparison with the first number, lower second number of coefficients to be ascertained by a second classification value, which represents a second, non-defective, state of health of the technical system.

8. The method as claimed in claim 4, further comprising:
prompting a first, high number of coefficients to be ascertained by a first classification value, which represents a first, defective, state of health of the technical system.

9. The method as claimed in claim 8, further comprising:
prompting a, in comparison with the first number, lower second number of coefficients to be ascertained by a second classification value, which represents a second, non-defective, state of health of the technical system.

10. The method as claimed in claim 8, wherein at least one of (i) the first number of coefficients and (ii) the second number of coefficients of an autoregressive model is determined by the Akaike information criterion.

11. The method as claimed in claim 10, further comprising:
performing an ascertainment of reconstructed data from the compressed data record.

12. The method as claimed in claim 11, wherein a projected spectrum is ascertained from a number of coefficients in the compressed data record per timestamp.

13. The method as claimed in claim 8, wherein at least one of (i) the first number of coefficients and the second number of coefficients of the autoregressive model is determined by a Bayesian information criterion.

14. The method as claimed in claim 8, wherein at least one of (i) the first number of coefficients and (ii) the second number of coefficients of the autoregressive model is determined such that at least one of (i) the first number of coefficients and (ii) the second number of coefficients corresponds to a number of frequencies.

15. The method as claimed in claim 4, further comprising:
prompting a, in comparison with the first number, lower second number of coefficients to be ascertained by a second classification value, which represents a second, non-defective, state of health of the technical system.

16. The method as claimed in claim 15, wherein at least one of (i) the first number of coefficients and (ii) the second number of coefficients of an autoregressive model is determined by the Akaike information criterion.

17. The method as claimed in claim 15, wherein at least one of (i) the first number of coefficients and the second number of coefficients of the autoregressive model is determined by a Bayesian information criterion.

18. The method as claimed in claim 15, wherein at least one of (i) the first number of coefficients and (ii) the second number of coefficients of the autoregressive model is determined such that at least one of (i) the first number of coefficients and (ii) the second number of coefficients corresponds to a number of frequencies.

19. The method as claimed in claim 18, wherein the projected spectrum is ascertained for at least one of the timestamps.

20. A non-transitory computer-readable medium which is loadable directly into internal memory of a digital signal processing unit and which comprises software code sections which, when executed on the digital signal processing unit causes compression of data representing a time-dependent signal comprising a multiplicity of time-dependent signal elements, the software code sections comprising:
program code for receiving a multiplicity of spectra, each spectrum of the multiplicity of spectra corresponding to one time-dependent signal element of the time-dependent signal elements, each spectrum comprising a multiplicity of frequencies and a multiplicity of amplitudes of the multiplicity of frequencies;
program code for generating a compressed data record;
program code for ascertaining a respective number of coefficients of an autoregressive model for a multiplicity of amplitudes of each of the multiplicity of frequencies; and
program code for generating the compressed data record, said compressed data record comprising at least a number of coefficients and the frequencies associated with the coefficients.

21. A signal processing unit for compressing data comprising:
a reception unit for receiving a multiplicity of spectra;
an autoregressive coefficient determination unit for determining a respective number of coefficients of an autoregressive model for a multiplicity of amplitudes of each frequency of the multiplicity of spectra; and
a memory unit for storing a compressed data record;
wherein the signal processor is configured to:
receive the multiplicity of spectra, each spectrum of the multiplicity of spectra corresponding to one time-dependent signal element of the time-dependent signal elements, and each spectrum comprising a multiplicity of frequencies and a multiplicity of amplitudes of the multiplicity of frequencies;
generate a compressed data record;
ascertain a respective number of coefficients of an autoregressive model for a multiplicity of amplitudes of each of the multiplicity of frequencies; and
generate the compressed data record, said compressed data record comprising at least a number of coefficients and the frequencies associated with the coefficients.

22. The signal processing unit as claimed in claim 21, further comprising:

a correlation unit for determining a correlation coefficient between the data and the reconstructed data.

23. The signal processing unit as claimed in claim 21, further comprising:
a spectrum unit for each of the time dependent signal elements for computing the respective spectrum.

\* \* \* \* \*